(12) United States Patent
Boute et al.

(10) Patent No.: US 8,298,153 B2
(45) Date of Patent: Oct. 30, 2012

(54) SYSTEM AND METHOD FOR THE DETECTION OF ACUTE MYOCARDIAL INFARCTION

(75) Inventors: Willem Boute, Brummen (NL); Jos van Hove, Vlaardingen (NL); David Robert Hampton, Woodinville, WA (US); Wilbert Wesselink, Doesburg (NL)

(73) Assignee: Medtronic, Inc., Minneapolis, MN (US)

( * ) Notice: Subject to any disclaimer, the term of this patent is extended or adjusted under 35 U.S.C. 154(b) by 1044 days.

(21) Appl. No.: 12/170,379

(22) Filed: Jul. 9, 2008

(65) Prior Publication Data
US 2010/0010358 A1    Jan. 14, 2010

(51) Int. Cl.
*A61B 5/02* (2006.01)
(52) U.S. Cl. .................................................. 600/508
(58) Field of Classification Search ............... 600/508
See application file for complete search history.

(56) References Cited

U.S. PATENT DOCUMENTS

| 6,217,525 | B1 * | 4/2001 | Medema et al. ............... 600/508 |
| 6,609,023 | B1 * | 8/2003 | Fischell et al. ................ 600/515 |
| 6,942,622 | B1 | 9/2005 | Turcott |
| 2003/0050566 | A1 | 3/2003 | Ujhelyi et al. |
| 2004/0039265 | A1 | 2/2004 | Bardy |
| 2004/0122478 | A1 | 6/2004 | Stadler et al. |
| 2005/0076909 | A1 | 4/2005 | Stahmann et al. |
| 2006/0106322 | A1 | 5/2006 | Arand et al. |
| 2006/0282000 | A1 | 12/2006 | Zhang et al. |
| 2007/0299356 | A1 | 12/2007 | Wariar et al. |
| 2008/0033303 | A1 | 2/2008 | Wariar et al. |
| 2008/0228094 | A1 | 9/2008 | Audet et al. |

FOREIGN PATENT DOCUMENTS

| WO | 03/020367 A1 | 3/2003 |
| WO | 2004/103150 A2 | 12/2004 |

OTHER PUBLICATIONS (PCT/US2009/04874) International Search Report and Written Opinion, 14 pages, Oct. 28, 2009.
Gersh, Bernard J., "Pharmacological Facilitation of Primary Percutaneous Coronary Intervention for Acute Myocardial Infarcation," JAMA, Feb. 23, 2005, vol. 293, No. 8, pp. 979-986.
Goldberg, Robert J. "Duration of, and Temporal Trends (1994-1997) in, Prehospital Delay in Patients With Acute Myocardial Infarction: The Second National Registry of Myocardial Infarction," Archives of Internal Medicine, Oct. 1999; vol. 159, pp. 2141-2147.

\* cited by examiner

*Primary Examiner* — Carl H Layno
*Assistant Examiner* — Yun Haeng Lee
(74) *Attorney, Agent, or Firm* — Stephen W. Bauer; Michael J. Ostrom

(57) ABSTRACT

A system and method are provided for the detection of acute myocardial infarction (AMI) using a staged approach for accurate and rapid detection. Physiological signals in a patient's body are sensed and corresponding physiological parameters are derived in a staged approach in order to determine the probability that AMI is occurring in a patient in a first detection stage. If the computed probability from physiological signals indicates the possibility of AMI, then the patient is prompted, such as through a patient-wearable device, to answer specific AMI-related questions to assist in diagnosis of AMI in a second stage. AMI is detected when the computed probability in the second stage exceeds a predefined detection threshold. A patient or physician alert may then be generated, which may further include the transfer of data via a communication link or network, in response to an AMI detection signal.

20 Claims, 5 Drawing Sheets

SYSTEM AND METHOD FOR THE DETECTION OF ACUTE MYOCARDIAL INFARCTION

TECHNICAL FIELD

This disclosure relates generally to medical devices and more particularly to a system and method for detecting acute myocardial infarction.

BACKGROUND

Historically, acute myocardial infarction (AMI) has been diagnosed in a patient when at least two of the following three criteria are satisfied: (1) ischemic chest pain typically associated with AMI, (2) electrocardiogram (ECG) findings typically associated with AMI (e.g., ST segment elevation and pathological Q-waves), and (3) raised concentrations of the enzyme creatine kinase (CK) in serum. It has been difficult for prior medical devices, either implantable or external, to detect AMI with satisfactory levels of sensitivity and specificity using the above three criteria. This difficulty in detection has led to the late recognition of AMI and action by the patient in seeking assistance, thereby leading to long delays until therapies are delivered to the patient, such as fibrinolysis or percutaneous coronary intervention (PCI).

SUMMARY

In one or more embodiments, a system and method are provided for the detection of acute myocardial infarction (AMI) or other physiological diseases using a staged approach for accurate and rapid detection. The method includes sensing at least one physiological signal in a patient's body and deriving a corresponding physiological parameter from each sensed signal in a first AMI detection stage. The probability of AMI is computed from the physiological parameter(s) in the first stage. If the computed probability indicates the possibility of AMI, then additional information is collected in a second stage in order to reach a predefined level of confidence of the detection of AMI. Once a predefined level of confidence is reached that AMI is being detected, the event is classified as AMI. In one or more embodiments, the collection and analysis of additional information in the second stage is performed within a predetermined time period after the computed probability indicates the possibility of AMI in the first stage.

In one or more embodiments, the additional information collected in the second stage relates to the acute myocardial infarction and supplements the physiological parameter derived in the first stage. In one or more embodiments, the additional information collected in the second stage includes at least one additional physiological signal that is sensed, where a corresponding physiological parameter is derived from each additional sensed physiological signal. In one or more embodiments, the additional information collected in the second stage information collected from a patient relates to acute myocardial infarction-related symptoms being experienced by the patient. The patient-provided information may be collected in response to a specific AMI-related query that is delivered to the patient after the computed probability of AMI reaches the sufficient threshold in the first stage. A probability of AMI is then computed from the collected additional information in the second stage. AMI is determined to likely be occurring in the patient when the computed probability in the second stage exceeds a predefined detection threshold. In some embodiments, the method includes generating a patient or physician alert or other report in response to an AMI detection.

The system for AMI detection may be implemented in an implantable or external medical device or a combination thereof. The system includes one or more physiological sensors coupled to signal processing controller for deriving multiple physiological parameters. The system further includes processing circuitry for receiving the physiological parameters, computing an AMI probability using the physiological parameters in a plurality of stages, and prompting an external patient-accessible device to query the patient about AMI-related symptoms. The system further includes processing circuitry for receiving the patient's responses to the query, and may further include components for generating an alert if a predefined level of confidence has been reached confirming the detection of AMI based on the combination of physiological parameters and patient-provided responses. The alert may include a patient or physician alert, which may further include the transfer of data via a communication link or network, in response to an AMI detection signal. In other embodiments, the system may further include therapy control and delivery circuitry for delivering a therapy to the patient in response to an AMI detection signal.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The invention provides a method and apparatus for detecting acute myocardial infarction and providing a response thereto. The invention may be implemented in implantable medical devices (IMDs) that include sensing capabilities for monitoring physiological conditions and may include therapy delivery capabilities. An IMD in which the invention is implemented may be primarily intended for detecting acute myocardial infarction purposes or may primarily be intended for other purposes. For example, the IMD may comprise any type of implanted device including, but not limited to cardiac pacemakers, implantable cardioverter-defibrillators (ICDs), implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patient. Telemetry is used to communicate sensed information from the IMD to an external medical device so that analysis of the sensed information can be performed. Telemetry is further used to communicate information or instructions from external medical devices to the IMD.

The invention may also be implemented in external medical devices that may be used for monitoring of a patient for detecting AMI at a variety of locations, such as a patient's home, a physician's office, a hospital or a treating emergency technician. In the description that follows, various embodiments of the invention are described relating to the detection of AMI. The methods and system provided by the present invention, however, are not limited to the detection of AMI but may be extended to the detection of other types of heart disease or other physiological diseases and conditions by monitoring respective physiological conditions.

Figure 1:
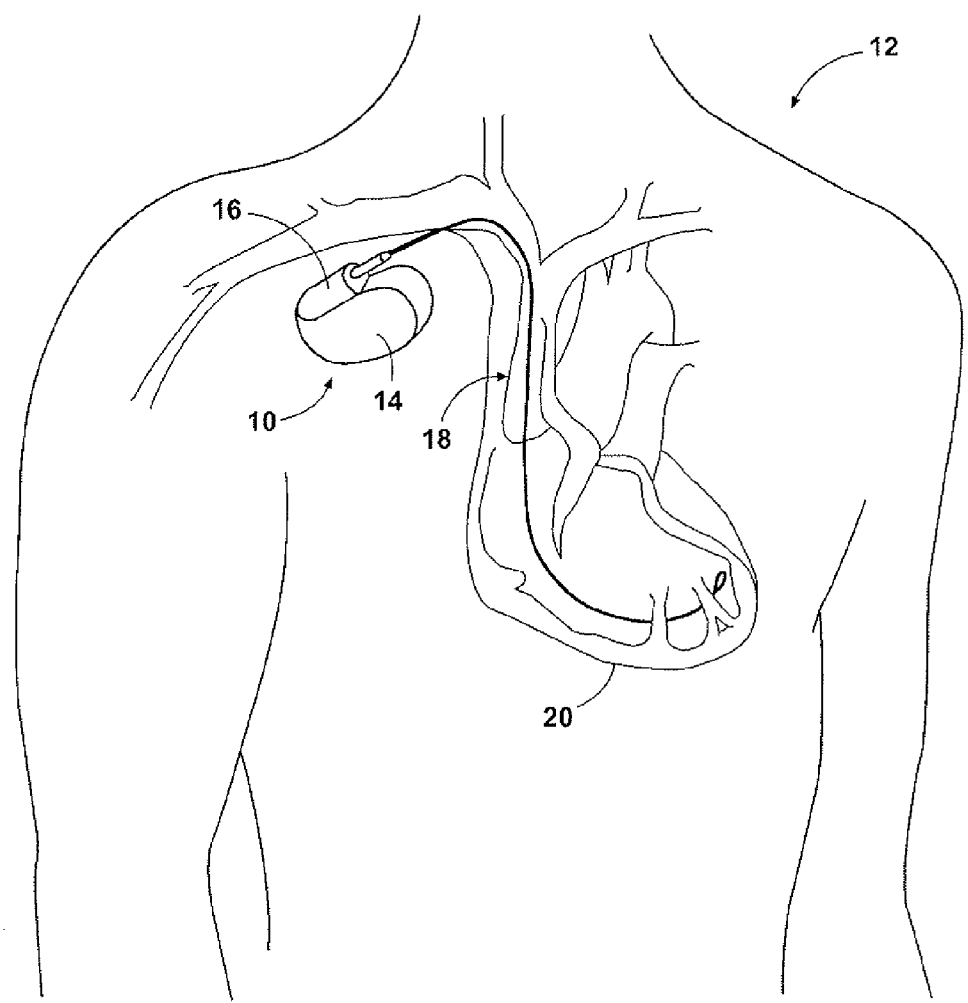
FIG. 1 illustrates an implantable medical device in accordance with an embodiment of the present disclosure implanted in a human body.

FIG. 1 is a simplified schematic view of one type of implantable medical device ("IMD") 10 implanted within a human body 12 in which one or more embodiments of the invention may be implemented. IMD 10 comprises a hermetically sealed enclosure 14 and connector module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device. For example, IMD 10 may include a lead-less subcutaneous device without actual electrical lead connections to the heart muscle or may include other types of implanted, subcutaneous and/or external medical devices and systems. IMD 10 collects and processes data from the patient for deriving parameters used in computing a probability that an AMI is occurring in the patient in which IMD 10 is implanted.

Figure 2:
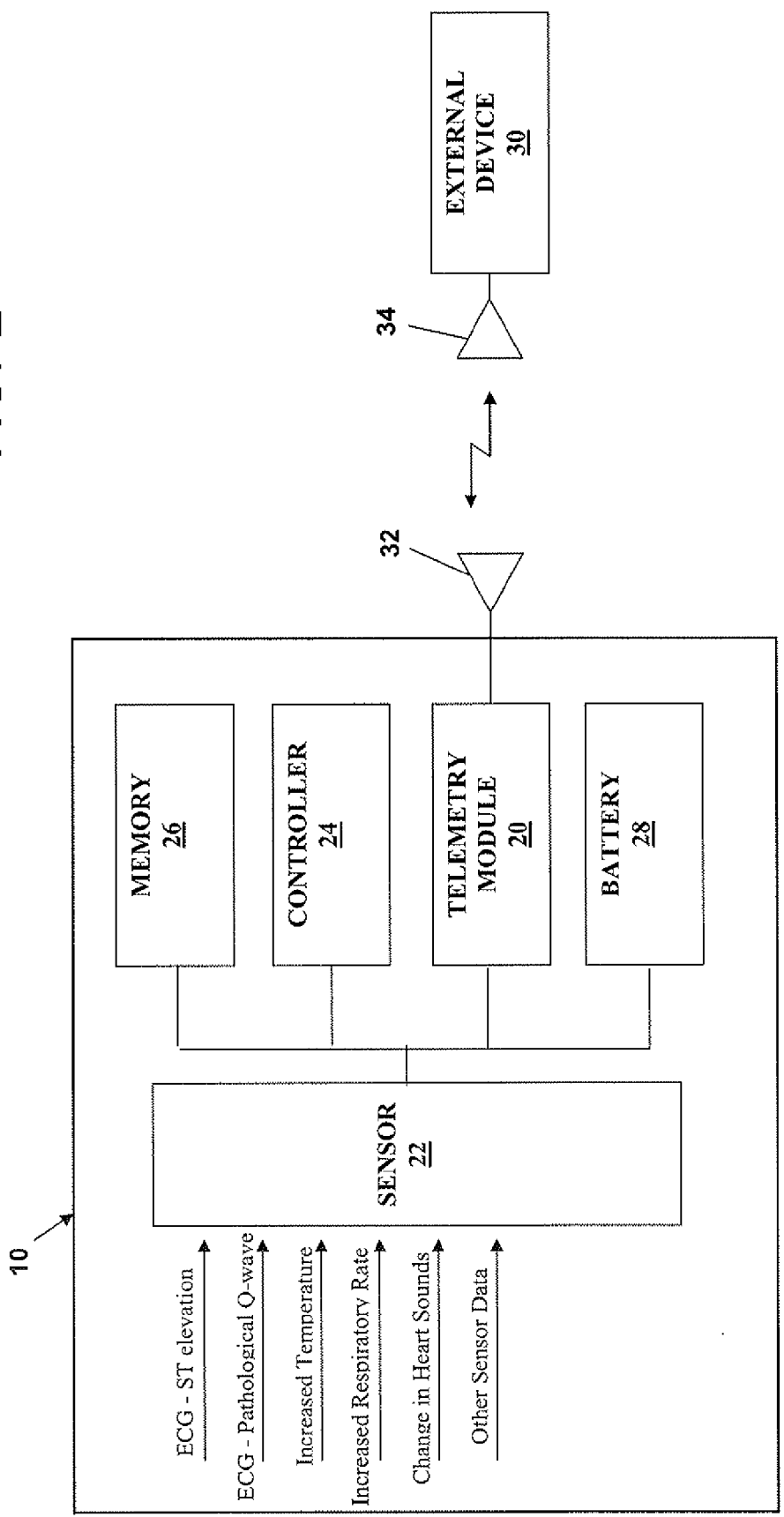
FIG. 2 is a block diagram illustrating the various components of one embodiment of an implantable medical device configured to operate in accordance with the present disclosure.

FIG. 2 is a block diagram illustrating the constituent components of IMD 10 in accordance with one or more embodiments having a microprocessor-based architecture. IMD 10 is shown as including telemetry module 20, at least one sensor 22, processor or controller 24, memory 26, battery 28 and other components as appropriate to produce the desired functionalities of the device.

Controller 24 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 24 executes instructions stored in memory 26 to provide functionality as described herein. Instructions provided to controller 24 may be executed in any manner, using any data structures, architecture, programming language and/or other techniques. Memory 26 is any storage medium capable of maintaining digital data and instructions provided to controller 24 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium.

As further shown in FIG. 1, IMD 10 may receive one or more cardiac leads 18 for connection to circuitry enclosed within the housing 14. In one or more embodiments, IMD 10 collects electrocardiogram (ECG) signals for use in deriving one or more heart rate related parameters, such as ST segment elevation, pathological Q-waves or other parameters for use in detecting AMI, as known to those skilled in the art. Other auxiliary leads may further be connected to both IMD 10 and the patient's body for detecting other physiological conditions, such as respiratory changes (e.g., respiratory rate, breathing depth, minute ventilation, etc.) through impedance changes, changes in the myocardial contraction pattern (e.g., as detected by changes in heart sound), body temperatures and other physiological conditions. The use of impedance signals for monitoring respiration rate and minute ventilation is known in the art, for example in rate responsive cardiac pacemakers.

Cardiac leads 18 may include, for example, pacing electrodes and defibrillation coil electrodes (not shown) in the event IMD 10 is configured to provide pacing, cardioversion and/or defibrillation. In addition, cardiac leads 18 may deliver pacing stimuli in a coordinated fashion to provide pacing pulses, cardiac resynchronization, extra systolic stimulation therapy or other benefits.

In operation, IMD 10 obtains data via electrodes and/or sensors 22 deployed on leads 18 and/or other sources. This data is provided to controller 24, which suitably analyzes the data, stores appropriate data in memory 26, and/or provides a response or report as appropriate. Any parameters indicating a likelihood of the occurrence of an AMI event can lead to further investigation by IMD 10 or can be responded to by intervention of a physician or in an automated manner. In various embodiments, IMD 10 prompts a patient to respond to specific questions that further assist in the detection of AMI and may activate an alert upon determination of AMI with sufficient specificity. Alternatively or in addition to alert activation, IMD 10 may select or adjust a therapy and coordinate the delivery of the therapy by IMD 10 or another appropriate device, which could be another IMD or an external device adapted to communicate with IMD 10 and respond to instructions received from IMD 10 or an external device.

Communication between IMD 10 and another device can occur via telemetry, such as a long-distance telemetry system through the telemetry module 20. Telemetry module 20 may comprise any unit capable of facilitating wireless data transfer between IMD 10 and an external device 30, where external device 30 may comprise an external medical device, a programming device, a remote telemetry station, a physician-activated device, a patient-activated device, a mobile handheld unit (e.g., mobile phone, PDA, etc.), a personal computer, an in-home monitoring device, a patient-wearable device, a display device or any other type of device capable of sending and receiving signals to and from IMD 10. Telemetry module 20 and external device 30 are respectively coupled to antennas 32 and 34 for facilitating the wireless data transfer.

Telemetry module 20 may be configured to perform any type of wireless communication. For example, telemetry module 20 may send and receive radio frequency (RF) signals, infrared (IR) frequency signals, or other electromagnetic signals. In the case of electromagnetic signals, antennas 32 and 34 may comprise coils for transmitting and receiving signals when positioned adjacent to one another. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and external device 30. Other types of wired communications may also occur when IMD 10 is alternatively configured as an external medical device or contains wired communication channels that extend from within the patient to points outside of the patient.

IMD 10 includes at least one sensor 22 configured to sense at least one physiological signal or condition, from which a physiological parameter can be determined. Sensors 22 can monitor electrical, mechanical, chemical, or optical information that contains physiological data of the patient and can utilize any source of physiological signals used for detecting AMI or any other physiological event or condition. In one or more embodiments, sensor 22 is configured to collect electrocardiogram (ECG) signals for use in deriving one or more heart rate related parameters, such as ST segment elevation, pathological Q-waves or other parameters for use in detecting AMI. For example, sensor 22 may comprise a heart sensor, such as the MDT Reveal® system, commercially available from Medtronic of Minneapolis, that is capable of sensing cardiac activity, electrocardiograms, heart rate, or the like. Reveal is a registered trademark of Medtronic, Inc. of Minneapolis, Minn.

In one or more embodiments, sensor 22 is configured to measure body temperatures of the patient. In one or more embodiments, sensor 22 is configured to sense respiratory changes, such as a change in respiratory rates, breathing depth, and/or minute ventilation. Respiration changes may be provided as an impedance signal obtained from cardiac electrodes or auxiliary electrodes, for example in the manner used for determining minute ventilation in rate responsive pacemakers or may alternatively be provided as any physiological signal that varies in response to the respiration cycle. In one or more embodiments, sensor 22 is configured to sense myocardial contraction pattern by detecting changes in heart sounds. In one or more embodiments, sensor 22 is configured to sense other physiological conditions useful in detecting AMI or other heart diseases or conditions. Increased temperatures, increased respiratory rates, and changes in heart sounds can all provide indications that an AMI is occurring in the patient.

Figure 3:
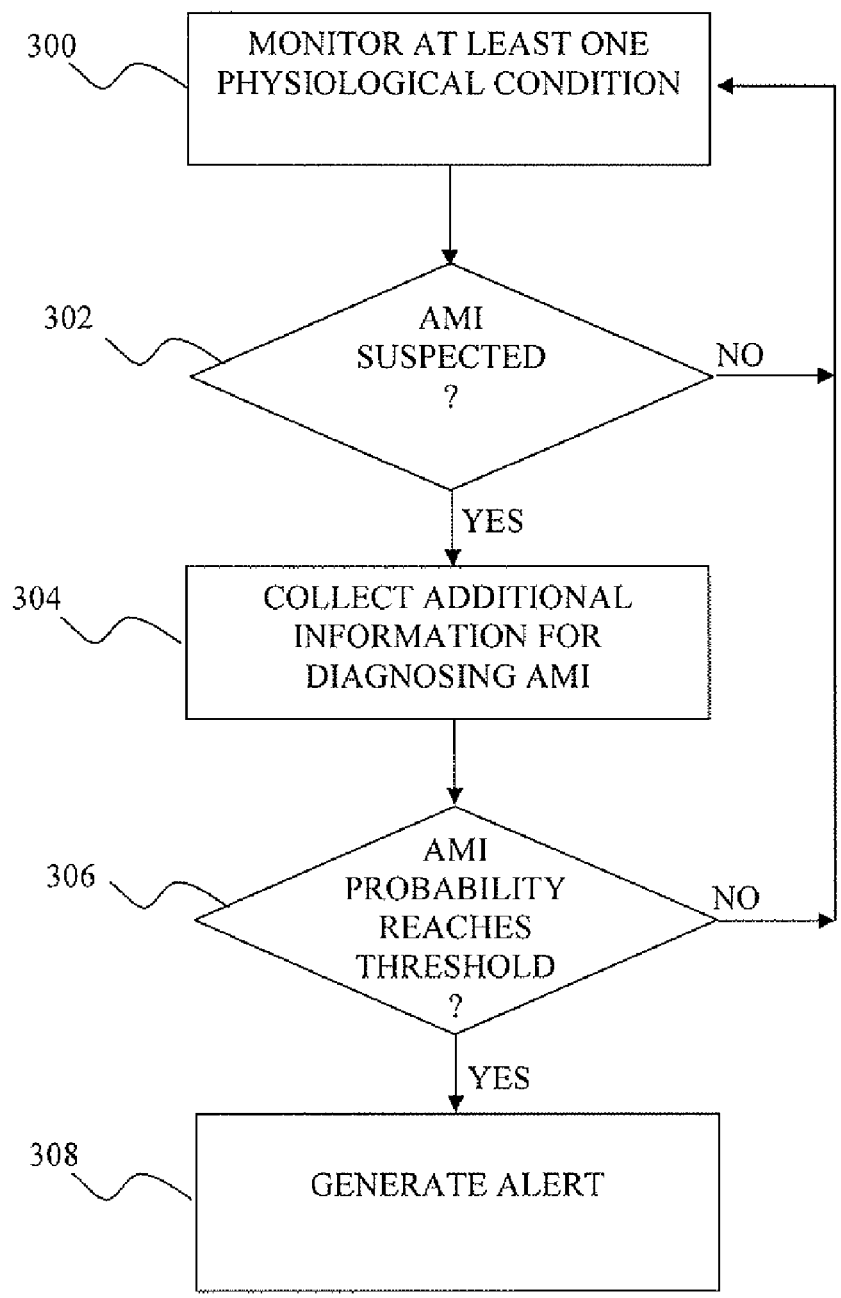
FIG. 3 is an operational flow diagram illustrating a process for performing the staged detection of acute myocardial infarction in accordance with one or more embodiments of the present disclosure.

Referring now to FIG. 3, an operation flow diagram is provided for one or more embodiments of detecting AMI using a staged approach in which subsequent stages of detection are performed to confirm the findings of previous stages until a desired level of specificity is achieved. AMI monitoring for detecting AMI according to the method of FIG. 3 may be performed continuously, or on a scheduled or triggered basis. For example, IMD 10 may be programmed to operate during certain hours or additionally or alternatively be enabled to be performed upon a triggering condition. A triggering condition may be an AMI indicator based on an activity signal or other physiological signal or any combination thereof.

AMI monitoring begins by sensing at least one physiological signal or condition useful in detecting AMI at step 300. Each of these signals may be sensed simultaneously to allow multiple, concurrent physiological parameter values to be determined for use in AMI detection or may alternatively be performed sequentially in stages and processed as required for that particular stage of the staged detection method. In one embodiment, an ECG signal is initially monitored to detect ST elevation and/or pathological Q-waves that can be an indication that the patient is experiencing an AMI. If a determination is made at step 302 that the sensed physiological signal indicates a probability that an AMI may be suspected to be occurring, additional information is then collected at step 304 to confirm with greater specificity whether an AMI is occurring. In one or more embodiments, the additional collected information includes sensing additional physiological signals useful in detecting AMI to determine whether these additional physiological signals also support a finding that AMI is occurring in the patient. As described above, these additional physiological signals could provide an indication of increased body temperature, increased respiratory rate, a change in heart sounds and/or other indications of AMI.

In some embodiments, patients may not be experiencing any symptoms that would be useful in the diagnosis of a medical condition, where the additional collected information that would be used in the determination that the medical condition is occurring in the patient would then only include further analysis of the sensed additional physiological signals described above. However, in other embodiments, patients may be experiencing symptoms that could be useful in the diagnosis of a medical condition. In one or more of such embodiments, IMD 10 may further prompt a patient questionnaire to be presented to the patient for the patient to provide responses to questions that may help determine whether the patient is experiencing certain symptoms associated with AMI, such as typical ischemic chest pain. In one or more embodiments, the additional information collected at step 304 includes these responses provided by the patient in response to the questionnaire.

If it is determined at step 306 that the collection of information obtained from the various sources in the various stages indicates with a certain probability that the patient is experiencing AMI (e.g., the probability reaches a certain threshold), the event is classified as AMI and an alert or report can be generated in step 308. In some embodiments, the analysis of the sensed physiological signal performed in step 302 may indicate with sufficient probability that an AMI is occurring, such that it is not necessary to collect additional information in order to diagnose AMI and an alert may be generated immediately following such a determination in step 302. For example, the magnitude of the sensed physiological signal (e.g., the amplitude of the ST elevation is very large and sustained) may indicate in step 302 with sufficient certainty that AMI is occurring and an alert may be generated immediately. In one or more embodiments, the collection of additional information and analysis of such additional information associated with steps 304 and 306 are only performed within a predetermined time period after the computed probability indicates the possibility of AMI from step 302, such that the possibility of AMI being detected from step 302 is discarded if the additional collected information fails to confirm within such predetermined time period that a certain probability exists that the patient is experiencing AMI.

In one or more embodiments, the various procedures implemented in connection with steps 300-306 may further be performed in a more continuous and evolutionary methodology rather than being performed based on the stepwise triggering of discrete events. For example, the sensing of the at least one physiological signal or condition useful in detecting AMI at step 300 can be alternatively be performed substantially simultaneous with the collection of additional information in step 304. Still further, analysis of physiological parameters may be responsive to other physiological parameters, changes in patient activity or to suggested interventions. For example, initial ST deviations could trigger an analysis of heart sounds, but there could also be further analysis of the deviation of ST levels over time when making the second stage confirmatory diagnosis. The responsiveness of physiological parameters to changes in patient activity or to suggested interventions (e.g., taking nitrates, etc.) may also be a factor in the second stage confirmatory diagnosis in assessing the probability that the patient is experiencing AMI (e.g., if ST deviations resolve within minutes of taking nitrates, it may be determined that the patient is experiencing angina and not an AMI).

Figure 4:
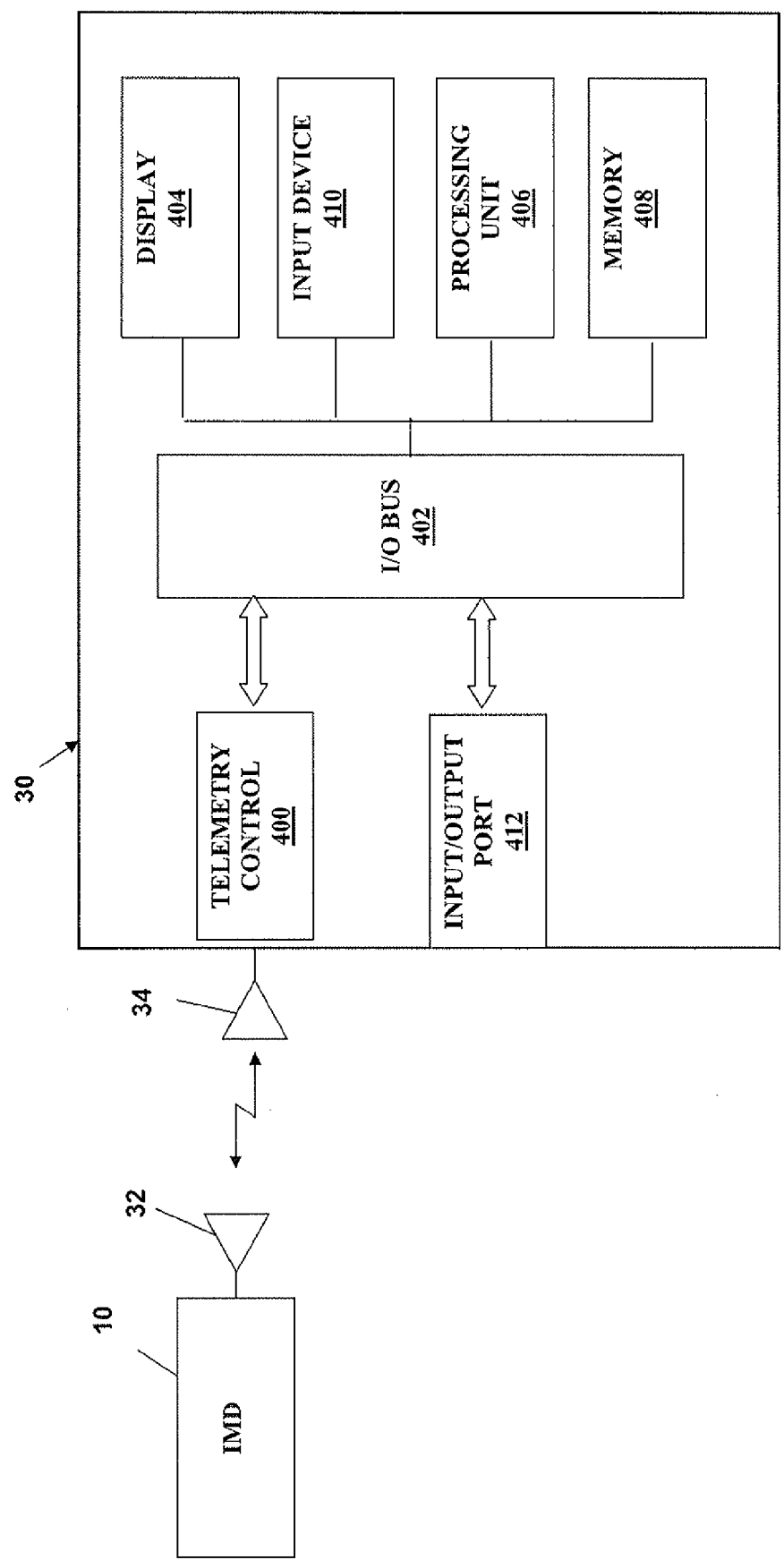
FIG. 4 is a block diagram illustrating the various components of one embodiment of an implantable medical device and external device configured to operate in accordance with one or more embodiments of the present disclosure.

In one or more embodiments, in order to prompt the patient with the patient questionnaire and collect additional information from the patient in connection with step 304, IMD 10 communicates instructions to external device 30 to prompt the patient with the patient questionnaire. External device 30 includes processing circuitry for interpreting data received from IMD 10 and presenting the questionnaire to the patient on a display of external device 30 or another device. Referring now to FIG. 4, a block schematic illustration of external device 30 is provided in accordance with one or more embodiments. External device 30 includes an antenna 34, coil or wired input for communicating data and other signals between external device 30 and IMD 10. Data is received from IMD 10 through antenna 34, which is connected to telemetry/antenna control circuit or module 400 that serves to demodulate telemetry signals received through antenna 34. The demodulated signals are applied in parallel or serial digital format to input/output (I/O) unit or bus 402, where they in turn may be applied to a display or screen 404, provided to processing unit 406 and/or memory 408. Processing unit 406 includes any type of microprocessor, digital signal processor, application specific integrated circuit (ASIC), field programmable gate array (FPGA) or other integrated or discrete logic circuitry programmed or otherwise configured to control operating of the external device 30 and provide functionality as described herein. In one embodiment, processing unit 406 executes instructions stored in memory 408 to provide functionality as described herein.

In one or more embodiments, external device 30 includes an input device 410 that allows data, commands or selections to be input into the external device 30 by a patient, physician or clinician. Input device 410 may include, but is not limited to, at least one of the following: a keyboard, track ball, mouse, touch-sensitive displays, push buttons, magnetic readers, RF readers, tablets, styluses, microphones, voice recognizers, handwriting recognizers and any other device that allows a patient, physician or clinician to input data to external device. Processing unit 406 controls operation of display 404 and is responsive to commands received from input device 410. Memory 408 is suitable for storing data received from IMD 10, input device 410, processing unit 406 or other data or commands otherwise received by external device 30. External device may further include an input/output port 412 for connecting external device 30 to other devices, communication networks, phone lines, wireless devices, etc. In one or more embodiments, external device 30 may relate information to the patient or a clinician by sound through speakers (not shown) in addition to or instead of presenting such information on display 404.

In one or more embodiments, external device 30 may be a portable device wearable or capable of being carried by the patient. In one or more embodiments, external device 30 may comprise an in-home monitoring device, such as the Medtronic CareLink® Network monitor, that collects information from IMDs implanted in patients and communicates such information to remote clinicians through the Internet, phone lines or wireless networks. Carelink is a registered trademark of Medtronic, Inc. of Minneapolis, Minn. In one or more embodiments, external device 30 may comprise a personal computer or mobile phone having a software program installed thereon configured for receiving data from IMD 10, processing such data and/or further communicating such data to a remote location or clinician for further analysis and/or processing.

When prompting the patient for additional information relating to more specific diagnosis of AMI, the patient is provided at least one question on display 404 that the patient provides responses to through input device 410 or the patient is otherwise provided with the opportunity to input specific information relevant to the diagnosis of AMI. For example, the patient can describe specific symptoms (e.g., typical ischemic chest pain) and locations of symptoms that can be used as a factor in the further diagnosing AMI with greater specificity. The information contained in the patient's responses can either be used directly by external device 30 in arriving at a determination that AMI is likely occurring or the information can be transmitted back to IMD 10 for further processing or to a remote location (e.g., the physician's office, hospital or another clinician) for further processing and analysis.

When a determination that AMI is occurring in the patient has been made with sufficient specificity and confidence according to a predefined threshold, an alert signal may be generated in step 308 that results in the telemetry uplink of data obtained from the various sensors 22 in IMD 10 to the networked external device 30 (such as a home monitor, personal computer, or cell phone). External device 30 receiving the wireless message may be a programmer/monitor device that advises the patient, a physician, a clinician or other attendant of the detected AMI or related data. Information stored in memory 26 of IMD 10 may be provided to external device 30 or another device to aid in diagnosis or treatment of the patient. Alternatively, external device 30 may be an interface to a communications network such that IMD 10 is able to transfer AMI-related detection data to an expert patient management center. External device 30 may transmit data to an expert data management center programmed to process the data and retrieve relevant information for distribution to a clinician, medical center, and/or back to the patient.

In one or more embodiments, external device 30 should be capable of prompting the patient to answer AMI specific questions during a respective stage of AMI detection. When the sensed physiological conditions and patient's responses to the questionnaire provide a likelihood that the patient is experiencing AMI, external device 30 may be capable of transmitting an alert to the patient, physician, call center, hospital, emergency response team or any other relevant party. The transmitted alert may include previously stored samples of measured physiological conditions and signals, real-time signals from the various sensors 22, and/or the patient's responses to the AMI questionnaire. In one or more embodiments, external device 30 may be programmed to further instruct the patient, emergency response personnel and/or bystanders to take appropriate actions to treat the AMI, where such instructions could be part of a bi-directional communication that occurs with paramedics/physicians that were alerted of the AMI. In one or more embodiments, external device 30 may send instructions or commands to IMD 10 to activate different measurements, collect and send additional data stored in memory 26 of IMD 10 to external device 30, or administer therapy to the patient.

Figure 5:
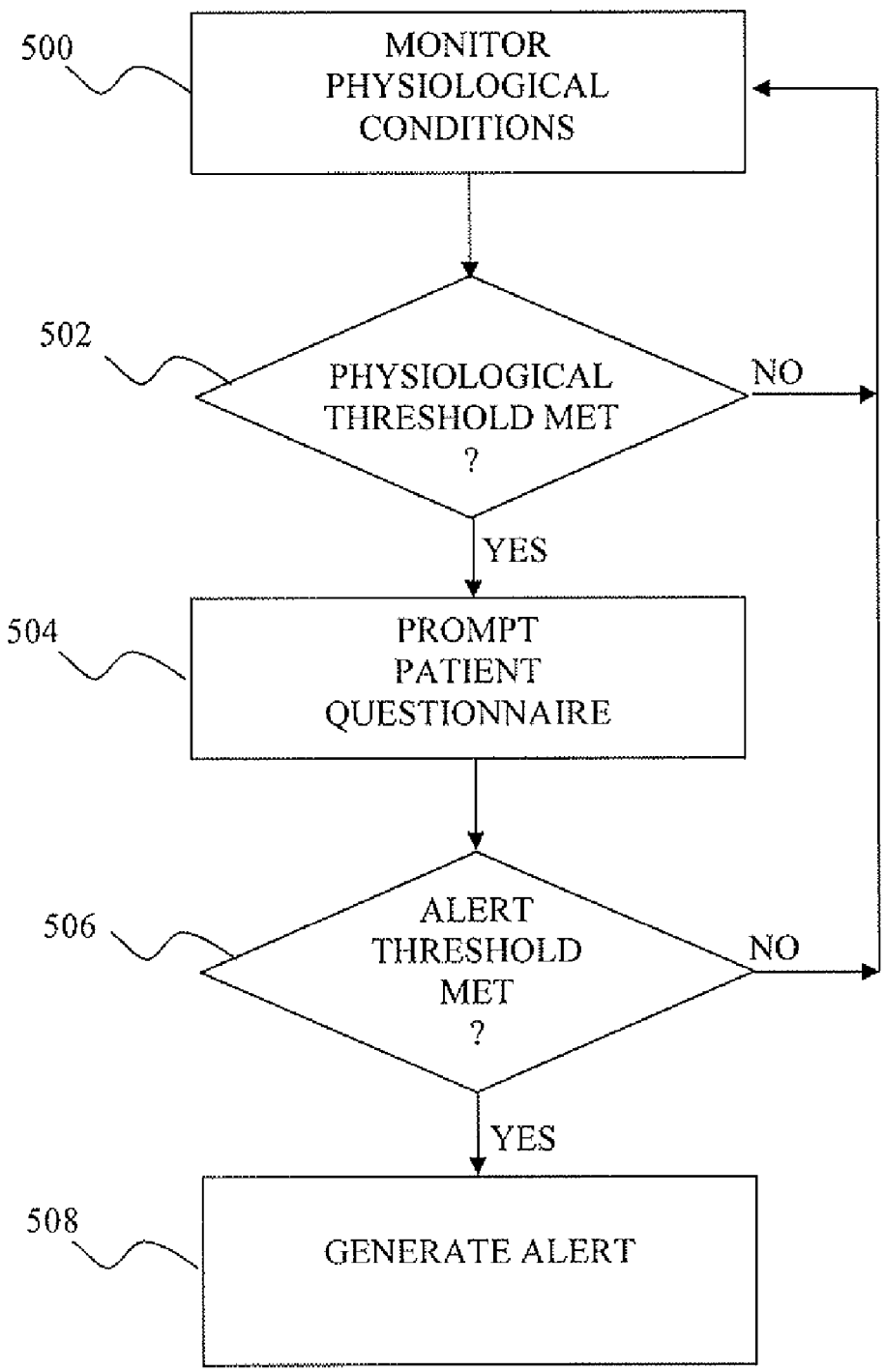
FIG. 5 is an operational flow diagram illustrating a process for performing the staged detection of acute myocardial infarction in accordance with one or more embodiments of the present disclosure.

Referring now to the operational flow diagram of FIG. 5, a further staged approach for detecting AMI is illustrated in accordance with one or more embodiments. AMI monitoring begins by sensing at least one physiological signal or condition useful in detecting AMI at step 500. Each of these signals may be sensed simultaneously to allow multiple, concurrent physiological parameter values to be determined for use in AMI detection or may alternatively be performed sequentially and processed in stages to provide added degrees of probability of detecting that AMI is occurring with each stage. As described herein, the monitored physiological signals from which physiological parameters are derived may include, but are not limited to, ECG signals to detect ST elevation and/or pathological Q-waves, temperature signals to detect increased body temperature, respiratory rate-related signals for detecting increased respiratory rates, myocardial contraction patterns for detecting changes in heart sounds, etc.

A determination is made at step 502 whether the sensed physiological signal(s) meets a predefined threshold for the physiological signal(s) indicating a probability that an AMI may be occurring. In one or more embodiments, the particular physiological signals that are monitored are performed in stages where additional monitoring stages of additional physiological signals are only performed if a monitored physiological signal from a prior stage indicates a probability that an AMI may be occurring. The number of physiological signals and the corresponding number of stages should be selected to be performed to provide a desired level of confidence that an accurate determination of whether AMI is occurring has been achieved. In one or more embodiments, each of the stages of monitoring of physiological signals can be performed until all desired physiological signals have been monitored regardless of the results related to the monitoring of each independent physiological signal.

The predefined threshold may comprise a single threshold value related a single or combination of sensed physiological signals, a plurality of threshold values with each respectively related to one of a plurality of physiological signals, and/or weighted thresholds that are weighted for respective stages of the physiological signal monitoring. Once it is determined that the physiological signal threshold is met, IMD 10 instructs external device 30 to prompt the patient in step 504 with the questionnaire to assist in the further diagnosis of the AMI event.

A determination is made in step 506 whether to generate an alert based on the patient's responses or particular symptoms the patient inputs into external device 30. The determination as whether to generate an alert may also use the monitored physiological sensor data as an additional basis in combination with the patient's responses to the questionnaire. The determination may be made by external device 30, IMD 10, another connected device or any combination thereof.

The method and apparatus for detecting acute myocardial infarction and providing a response thereto described in the various embodiments herein allow AMI to be detected using a staged approach to minimize power consumption in an IMD, to preserve physiological sensor life (especially in the case of electrochemical sensors), and enhance net screening specificity for medical conditions by limiting the number of sensor inputs with associated false-positive probabilities. The method and apparatus for detecting acute myocardial infarction and providing a response thereto described in the various embodiments herein further allow AMI to be diagnosed in near real-time to when AMI is initially experienced by a patient. This allows therapies and responses to be delivered to the patient without significant delay, thereby adding to likelihood of the effectiveness of the therapy and treatment provided to the patient. Further, by implementing a staged approach for detecting AMI by performing stages of physiological signal monitoring, a predefined level of confidence that AMI is being detected can be achieved before alerts or additional stages of detection are performed, thereby minimizing the probabilities of generating false alerts. Still further, by prompting a patient to enter a number of AMI related questions immediately upon physiological signals providing an indication of AMI, typical ischemic chest pain can be diagnosed and used in detecting AMI at an early stage before a patient may typically bring such pains to the attention of a physician. Conventionally, it has been difficult for a patient to associate such symptoms with the occurrence of an AMI, whereas the present system and method allow the patient's symptoms to immediately be diagnosed through the triggering of sensed physiological parameters to provide an indication of an AMI occurrence.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
sensing at least one physiological signal in a first stage;
deriving a corresponding physiological parameter from each sensed signal in the first stage;
computing a probability of acute myocardial infarction from the physiological parameters in the first stage;
determining that the computed probability of acute myocardial infarction has reached a sufficient threshold in the first stage;
in response to the determination that the computed probability of acute myocardial infarction reached the sufficient threshold in the first stage, collecting additional information related to acute myocardial infarction in a second stage;
computing a probability of acute myocardial infarction from the collected additional information in the second stage; and
classifying an event as acute myocardial infarction when the computed probability in the second stage exceeds a predefined detection threshold.

2. The method of claim 1, further comprising collecting additional information in the second stage by sensing at least one additional physiological signal and deriving a corresponding physiological parameter from each additional sensed signal.

3. The method of claim 1, further comprising collecting additional information in the second stage by collecting information from a patient relating to acute myocardial infarction-related symptoms being experienced by the patient.

4. The method of claim 3, further comprising querying the patient with acute myocardial infarction-related questions in response to the computed probability of acute myocardial infarction reaching the sufficient threshold in the first stage.

5. The method of claim 1, wherein the physiological signals comprise at least one of a cardiac electrical signal, a respiratory signal, a temperature signal and a heart sound signal.

6. The method of claim 1, further comprising generating an alert when the computed probability in the second stage exceeds a predefined detection threshold.

7. The method of claim 1, further comprising:
performing the sensing, deriving and computing actions of the first stage in an implantable medical device implanted in a patient; and
performing the collecting, computing and detecting actions of the second stage in a device external to the patient and in communication with the implantable medical device.

8. A system comprising:
at least one physiological sensor configured to sense a corresponding physiological signal;
a controller configured to derive a corresponding physiological parameter from each sensed signal, to compute a probability of acute myocardial infarction from the physiological parameters in a first stage, and to determine that the computed probability of acute myocardial infarction has reached a sufficient threshold in the first stage;
the controller further configured to, in response to determining that the computed probability of acute myocardial infarction has reached the sufficient threshold in the first stage, collect additional information related to acute myocardial infarction in a second stage;
the controller further configured to compute a probability of acute myocardial infarction from the collected additional information in the second stage and to classify an event as acute myocardial infarction when the computed probability in the second stage exceeds a predefined detection threshold.

9. The system of claim 8, further comprising at least one additional physiological sensor configured to sense a corresponding additional physiological signal, wherein the controller is further configured to collect information in the second stage by sensing the at least one additional physiological signal and to derive a corresponding physiological parameter from each additional sensed signal.

10. The system of claim 8, wherein the controller is further configured in the second stage to initiate the collection of information from a patient relating to acute myocardial infarction-related symptoms being experienced by the patient.

11. The system of claim 10, wherein the controller is further configured to generate a command to an external device to query the patient with acute myocardial infarction-related questions in response to the computed probability of acute myocardial infarction reaching the sufficient threshold in the first stage.

12. The system of claim 8, wherein the at least one physiological sensor is configured to sense at least one of a cardiac electrical signal, a respiratory signal, a temperature signal and a heart sound signal.

13. The system of claim 8, wherein the controller is further configured to generate an alert when the computed probability in the second stage exceeds a predefined detection threshold.

14. A system comprising:
means for sensing at least one physiological signal in a first stage;
means for deriving a corresponding physiological parameter from each sensed signal in the first stage;
means for computing a probability of acute myocardial infarction from the physiological parameters in the first stage;
means for determining that the computed probability of acute myocardial infarction has reached a sufficient threshold in the first stage;
means for collecting additional information related to acute myocardial infarction in a second stage in response to the determination that the computed probability of acute myocardial infarction from the physiological parameters in the first stage reached the sufficient threshold;
means for computing a probability of acute myocardial infarction from the collected additional information in the second stage; and
means for classifying an event as acute myocardial infarction when the computed probability in the second stage exceeds a predefined detection threshold.

15. The system of claim 14, wherein the means for collecting additional information in the second stage senses at least one additional physiological signal and derives a corresponding physiological parameter from each additional sensed signal.

16. The system of claim 14, wherein the means for collecting additional information in the second stage collects information from a patient relating to acute myocardial infarction-related symptoms being experienced by the patient.

17. The system of claim 16, further comprising means for querying the patient with acute myocardial infarction-related questions in response to the computed probability of acute myocardial infarction reaching the sufficient threshold in the first stage.

18. The system of claim 14, wherein the means for sensing at least one physiological signal sense at least one of a cardiac electrical signal, a respiratory signal, a temperature signal and a heart sound signal.

19. The system of claim 14, further comprising means for generating an alert when the computed probability in the second stage exceeds a predefined detection threshold.

20. The system of claim 19, further comprising means for generating a response to the classification of an event as acute myocardial infarction when an alert is generated.

* * * * *